US008828366B2

(12) United States Patent
Bui et al.

(10) Patent No.: US 8,828,366 B2
(45) Date of Patent: Sep. 9, 2014

(54) HYDRATING CREAM FOUNDATION IN EMULSION FORM

(75) Inventors: Hy Si Bui, Piscataway, NJ (US); Mohamed Kanji, Edison, NY (US); Susan Halpern, Paramus, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/825,614

(22) Filed: Jun. 29, 2010

(65) Prior Publication Data

US 2010/0330012 A1    Dec. 30, 2010

Related U.S. Application Data

(60) Provisional application No. 61/221,299, filed on Jun. 29, 2009.

(51) Int. Cl.
| | | |
|---|---|---|
| *A61K 8/00* | (2006.01) | |
| *A61K 8/18* | (2006.01) | |
| *A61K 31/715* | (2006.01) | |
| *A61Q 3/00* | (2006.01) | |
| *A61Q 1/02* | (2006.01) | |
| *A61Q 19/04* | (2006.01) | |
| *A61Q 1/04* | (2006.01) | |
| *A61Q 1/06* | (2006.01) | |
| *A61Q 1/00* | (2006.01) | |
| *A61Q 5/00* | (2006.01) | |
| *A61K 8/81* | (2006.01) | |
| *A61K 8/73* | (2006.01) | |

(52) U.S. Cl.
CPC .............. *A61K 8/731* (2013.01); *A61K 8/8164* (2013.01); *A61K 2800/594* (2013.01); *A61Q 1/02* (2013.01)
USPC ................... 424/61; 424/63; 424/64; 514/57

(58) Field of Classification Search
USPC .......................... 424/61, 63, 64, 70.6; 514/57
See application file for complete search history.

(56) References Cited

U.S. PATENT DOCUMENTS

| | | |
|---|---|---|
| 2,957,838 A | 10/1960 | Mills, Jr. |
| 3,590,076 A | 6/1971 | Heintzelman et al. |
| 3,699,154 A | 10/1972 | Heintzelman et al. |
| 3,933,511 A | 1/1976 | Heintzelman et al. |
| 3,933,512 A | 1/1976 | Heintzelman et al. |
| 4,041,056 A | 8/1977 | Heintzelman et al. |
| 4,226,889 A | 10/1980 | Yuhas |
| 4,420,588 A | 12/1983 | Yoshioka et al. |
| 4,871,536 A | 10/1989 | Arraudeau et al. |
| 5,032,391 A | 7/1991 | Helioff et al. |
| 5,389,363 A | 2/1995 | Snyder et al. |
| 5,618,524 A | 4/1997 | Bolich et al. |
| 5,620,693 A | 4/1997 | Piot et al. |
| 5,800,816 A | 9/1998 | Brieva et al. |
| 5,911,974 A | 6/1999 | Brieva et al. |
| 5,965,112 A | 10/1999 | Brieva et al. |
| 5,985,298 A | 11/1999 | Brieva et al. |
| 5,998,547 A * | 12/1999 | Hohner .................. 525/301 |
| 6,126,929 A | 10/2000 | Mougin |
| 6,274,152 B1 | 8/2001 | Brieva et al. |
| 6,464,964 B1 | 10/2002 | Brieva et al. |
| 6,482,400 B1 | 11/2002 | Collin |
| 6,492,455 B1 | 12/2002 | Nadolsky |
| 6,524,564 B1 | 2/2003 | Kim et al. |
| 6,562,322 B2 | 5/2003 | Brieva et al. |
| 6,716,419 B2 | 4/2004 | Zoltowski et al. |
| 6,780,422 B2 | 8/2004 | Brieva et al. |
| 6,958,148 B1 | 10/2005 | Green et al. |
| 7,005,134 B2 | 2/2006 | Brieva et al. |
| 7,160,550 B2 | 1/2007 | Brieva et al. |
| 7,186,766 B2 | 3/2007 | Harashina et al. |
| 7,314,904 B2 | 1/2008 | Nadolsky et al. |
| 7,423,104 B2 | 9/2008 | Lion |
| 7,682,621 B2 | 3/2010 | Lamberty et al. |
| 7,875,265 B2 | 1/2011 | Blin et al. |
| 8,119,110 B2 | 2/2012 | Blin et al. |
| 8,551,461 B2 | 10/2013 | Bui et al. |
| 2003/0026816 A1 | 2/2003 | Zoltowski et al. |
| 2003/0082218 A1 | 5/2003 | Ichinohe et al. |
| 2003/0147931 A1 | 8/2003 | Brieva et al. |
| 2003/0182734 A1* | 10/2003 | Desenne et al. .................. 8/405 |
| 2004/0170586 A1 | 9/2004 | Ferrari et al. |
| 2004/0186308 A1 | 9/2004 | Koch et al. |
| 2004/0223986 A9 | 11/2004 | Boussouira et al. |
| 2005/0013992 A1 | 1/2005 | Azad et al. |
| 2005/0180936 A1 | 8/2005 | Pays |
| 2005/0220728 A1 | 10/2005 | Kanji et al. |

(Continued)

FOREIGN PATENT DOCUMENTS

| | | |
|---|---|---|
| DE | 100 64 799 A1 | 6/2002 |
| DE | 102004008941 A1 | 9/2005 |

(Continued)

OTHER PUBLICATIONS

Hauthal, Tenside Surf. Det. 2008, 45 (1), 3-42.*
U.S. Appl. No. 12/825,707, filed Jun. 29, 2010, Bui, et al.
U.S. Appl. No. 12/825,767, filed Jun. 29, 2010, Bui, et al.
U.S. Appl. No. 12/825,807, filed Jun. 29, 2010, Bui, et al.
U.S. Appl. No. 12/825,587, filed Jun. 29, 2010, Bui, et al.
U.S. Appl. No. 12/825,840, filed Jun. 29, 2010, Bui, et al.

(Continued)

*Primary Examiner* — Gina C Justice
*Assistant Examiner* — Genevieve S Alley
(74) *Attorney, Agent, or Firm* — Oblon, Spivak, McClelland, Maier & Neustadt, L.L.P.

(57) ABSTRACT

The present invention is directed to a cosmetic composition that is moisturizing, hydrating, refreshing and long wearing, and has an unique texture and feel comprising a cellulosic gelling agent, an oil-soluble polar modified polymer, and water.

19 Claims, No Drawings

(56) References Cited

U.S. PATENT DOCUMENTS

| | | |
|---|---|---|
| 2006/0013840 A1 | 1/2006 | Lamberty et al. |
| 2006/0074029 A1* | 4/2006 | Leece ............................ 514/23 |
| 2006/0084764 A1 | 4/2006 | Hanna et al. |
| 2006/0093568 A1 | 5/2006 | Blin et al. |
| 2006/0104940 A1 | 5/2006 | Heinrichs et al. |
| 2006/0110345 A1 | 5/2006 | Lu et al. |
| 2006/0115444 A1 | 6/2006 | Blin et al. |
| 2006/0147396 A1* | 7/2006 | Monello ......................... 424/59 |
| 2006/0147402 A1 | 7/2006 | Blin et al. |
| 2006/0159642 A1 | 7/2006 | Hanna et al. |
| 2006/0165626 A1 | 7/2006 | Ricard et al. |
| 2006/0188459 A1 | 8/2006 | Heinrichs et al. |
| 2007/0031361 A1* | 2/2007 | Herrmann et al. ......... 424/70.11 |
| 2007/0092468 A1 | 4/2007 | Brieva et al. |
| 2007/0110700 A1 | 5/2007 | Wells et al. |
| 2007/0110702 A1 | 5/2007 | Ehara |
| 2007/0134181 A1 | 6/2007 | Shimizu et al. |
| 2007/0212315 A1 | 9/2007 | Pastor et al. |
| 2007/0256700 A1 | 11/2007 | Bodelin |
| 2007/0258932 A1 | 11/2007 | Bui et al. |
| 2007/0259012 A1 | 11/2007 | Castro et al. |
| 2008/0025934 A1 | 1/2008 | Lebre et al. |
| 2008/0207871 A1 | 8/2008 | Seiler et al. |
| 2009/0060959 A1 | 3/2009 | Igarashi |
| 2009/0130037 A1 | 5/2009 | Thevenet et al. |
| 2010/0310489 A1 | 12/2010 | Barba |
| 2010/0330012 A1 | 12/2010 | Bui et al. |
| 2010/0330015 A1 | 12/2010 | Bui et al. |
| 2010/0330016 A1 | 12/2010 | Bui et al. |
| 2010/0330017 A1 | 12/2010 | Bui et al. |
| 2010/0330022 A1 | 12/2010 | Bui et al. |
| 2010/0330024 A1 | 12/2010 | Bui et al. |
| 2011/0020254 A1 | 1/2011 | Bui et al. |
| 2011/0020255 A1 | 1/2011 | Bui et al. |
| 2011/0020256 A1 | 1/2011 | Bui et al. |
| 2011/0020257 A1 | 1/2011 | Bui et al. |
| 2011/0020259 A1 | 1/2011 | Bui et al. |
| 2011/0020260 A1 | 1/2011 | Bui et al. |
| 2011/0020261 A1 | 1/2011 | Bui et al. |
| 2011/0020263 A1 | 1/2011 | Ilekti et al. |
| 2011/0021681 A1 | 1/2011 | Bui et al. |
| 2011/0021683 A1 | 1/2011 | Bui et al. |
| 2011/0038819 A1 | 2/2011 | Bui et al. |
| 2011/0223122 A1 | 9/2011 | Bui et al. |
| 2011/0223123 A1 | 9/2011 | Bui et al. |
| 2011/0280817 A1 | 11/2011 | Ramadan et al. |
| 2011/0280818 A1 | 11/2011 | Kawaratani et al. |
| 2011/0280819 A1 | 11/2011 | Bui et al. |
| 2011/0280820 A1 | 11/2011 | Bui et al. |
| 2011/0286949 A1 | 11/2011 | Bui et al. |
| 2011/0286950 A1 | 11/2011 | Bui et al. |
| 2011/0286951 A1 | 11/2011 | Bui et al. |
| 2011/0286954 A1 | 11/2011 | Bui et al. |
| 2011/0293550 A1 | 12/2011 | Bui et al. |
| 2011/0311467 A1 | 12/2011 | Bui et al. |
| 2012/0003169 A1 | 1/2012 | Bui et al. |
| 2012/0004327 A1 | 1/2012 | Bui et al. |
| 2012/0020907 A1 | 1/2012 | Bui et al. |
| 2012/0107263 A1 | 5/2012 | Bui et al. |
| 2012/0171137 A1 | 7/2012 | Bradsaw et al. |
| 2012/0171139 A1 | 7/2012 | Bradshaw et al. |
| 2012/0171140 A1 | 7/2012 | Bui et al. |
| 2014/0004069 A1 | 1/2014 | Bui et al. |
| 2014/0037565 A1 | 2/2014 | Bui et al. |

FOREIGN PATENT DOCUMENTS

| | | | |
|---|---|---|---|
| EP | 1 314 415 A1 | | 5/2003 |
| EP | 1 854 451 A2 | | 11/2007 |
| EP | 2 036 536 A1 | | 3/2009 |
| JP | A-07053921 | | 2/1995 |
| WO | WO 96/03967 A1 | | 2/1996 |
| WO | WO 01/17485 | | 3/2001 |
| WO | WO 02/088456 A1 | | 11/2002 |
| WO | WO 02 098379 A1 | | 12/2002 |
| WO | WO 2006/112690 A1 | | 10/2006 |
| WO | WO 2006/127883 A2 | | 11/2006 |
| WO | WO 2007/048672 | * | 5/2007 |
| WO | WO 2007/048672 A1 | | 5/2007 |
| WO | WO 2007/096400 A1 | | 8/2007 |
| WO | WO 2007/139812 A2 | | 12/2007 |
| WO | WO 2008/046763 | * | 4/2008 |
| WO | WO 2008/046763 A1 | | 4/2008 |
| WO | WO 2009/085888 A1 | | 7/2009 |

OTHER PUBLICATIONS

U.S. Appl. No. 12/825,623, filed Jun. 29, 2010, Bui, et al.
U.S. Appl. No. 12/825,726, filed Jun. 29, 2010, Bui, et al.
U.S. Appl. No. 12/825,633, filed Jun. 29, 2010, Bui, et al.
U.S. Appl. No. 12/825,599, filed Jun. 29, 2010, Bui, et al.
U.S. Appl. No. 12/825,816, filed Jun. 29, 2010, Bui, et al.
U.S. Appl. No. 12/825,730, filed Jun. 29, 2010, Bui, et al.
U.S. Appl. No. 12/825,600, filed Jun. 29, 2010, Bui, et al.
U.S. Appl. No. 12/825,559, filed Jun. 29, 2010, Bui, et al.
U.S. Appl. No. 13/133,176, filed Jun. 7, 2011, Bui, et al.
U.S. Appl. No. 13/133,181, filed Aug. 1, 2011, Bui, et al.
U.S. Appl. No. 13/379,691, filed Dec. 21, 2011, Bui, et al.
U.S. Appl. No. 14/147,726, filed Jan. 6, 2014, Bui, et al.
U.S. Appl. No. 14/241,361, filed Feb. 26, 2014, Motornov, et al.
U.S. Appl. No. 14/241,753, filed Feb. 27, 2014, Motornov, et al.
U.S. Appl. No. 14/227,264, filed Mar. 27, 2014, Bui, et al.
European Office Action Issued Feb. 22, 2013 in Patent Application No. 10 167 788.8.
Hauthal, H. G. Basics, Ingredients, Detergents, Product Safety and Sustainability. Tenside Surf. Del. Jan. 2008, 45 (I), 30-42.
Vertellus, ZeMac(R) E400 Copolymer Technical Data Sheet, May 29, 2008.
European Search Report dated Mar. 10, 2011, in European Application No. 10167784.7.
European Office Action from European Patent Application No. 10167784.7 dated Mar. 21, 2011 (4 pages).
L. Rudnick, Synthesis, Mineral Oils, and Bio-Based Lubricants, Chemistry and Technology.
Perstorp, Bohorn® H20 product data sheet dated Jan. 3, 2008.
Perstorp, Determination of Viscosity for Bottom Dendritic Polymers, Aug. 23, 2011.
Mulkem et al. Polymer, 2000, 41 (9), 3193-3203.
Bergbreiter et al. Tetrahedron Letters, 1997, 38 (21), 3703-3706.
European Search Report issued Apr. 8. 2011, in European Patent Application No. 10167791.2 (with English Abstract).
European Search Report issued Mar. 21, 2011, in European Application No. 10167792.0.
European Search Report issued Apr. 6, 2011, in European Patent Application No. 10167794.6.
European Search Report dated Mar. 14, 2011, issued in European Application No. 10167785.4.
European Patent Office Communication dated Apr. 18, 2011, issued in European Application No. 10167785.4.
European Search Report issued Mar. 10, 2011, in European Application No. 10167790.4.
European Office Action issued in European Patent Application No. 10167790.4 dated Mar. 21, 2011 (4 pages).
International Search Report issued May 20, 2010 in PCT/US09/067332 filed Dec. 9, 2009.
International Search Report issued Aug. 11, 2010 in PCT/US09/68246 filed Dec. 16, 2009.
International Search Report Issued Jul. 26, 2010 in PCT/US09/068151 filed Dec. 16, 2009.
International Search Report issued Jul. 28, 2010 in PCT/US09/68251 filed Dec. 16, 2009.
International Search Report issued Jul. 30, 2010 in PCT/US09/68148 filed Dec. 16, 2009.
http://www.Chemical Book.com/ChemicalProductProperty_EN_CB3748204.htm, Poly (methyl vinyl ether-alt-maleic anhydride), 2010.
International Search Report Issued Jul. 30, 2010 in PCT/US09/068146 filed Dec. 16, 2009.

(56) References Cited

OTHER PUBLICATIONS

International Search Report issued Jul. 23, 2010 in PCT/US09/68245 filed Dec. 16, 2009.
Extended European Search Report Issued Nov. 29, 2012 in Patent Application No. 08867867.7.

International Search Report issued May 31, 2010 in PCT/US09/067338 filed Decemher 9, 2009.
European Search Report issued Feb. 6, 2014 in European Patent Application No. 10167787.0.
Communication Pursuant to Article 94(3) EPC issued Mar. 10, 2014, in European Patent Application No. 10 167 787.0.

* cited by examiner

HYDRATING CREAM FOUNDATION IN EMULSION FORM

CROSS-REFERENCE TO RELATED APPLICATIONS

This application claims the benefit of priority from U.S. Provisional Application Ser. No. 61/221,299, filed Jun. 29, 2009, the entire contents of which are hereby incorporated by reference.

FIELD OF THE INVENTION

The present invention generally relates to a novel cream composition which is hydrating and refreshing and which has excellent long wearing properties.

BACKGROUND OF THE INVENTION

Many compositions, especially cosmetic compositions, have been developed for easy and comfortable application onto a targeted substrate. Unfortunately, many of these compositions are in fact difficult to apply and do not possess a smooth feel upon application. Moreover, compositions often have a tendency to feel tacky, yielding poor application and spreadability characteristics. Similarly, the use of silicone resins to impart transfer resistance onto a colored cosmetic product suffers from the same disadvantages disclosed above.

Therefore, it is desirable to provide a composition capable of possessing a creamy texture and feel with highly moisturizing and long wearing properties without the need for having to use expensive ingredients and/or processing techniques.

BRIEF SUMMARY OF THE INVENTION

A first aspect of the present invention is directed to a composition that includes: (a) at least one gelling agent chosen from cellulose and derivatives thereof; (b) at least one oil-soluble polar modified polymer; and (c) water.

A second aspect of the present invention is directed to a method of making up a keratinous substrate (for example, skin) comprising applying the above-disclosed composition onto the substrate in an amount sufficient to make-up the substrate.

It has been surprisingly discovered that the invention compositions display a high amount of moisturization to the keratinous substrate to which they have been applied and are longwearing despite the absence of silicone resins and traditional film formers. Further, the composition provides a unique texture and is stable.

DETAILED DESCRIPTION OF THE INVENTION

Other than in the operating examples, or where otherwise indicated, all numbers expressing quantities of ingredients and/or reaction conditions are to be understood as being modified in all instances by the term "about".

"Film former" or "film forming agent" or "film forming resin" as used herein means a polymer which, after dissolution in at least one solvent (such as, for example, water and organic solvents), leaves a film on the substrate to which it is applied, for example, once the at least one solvent evaporates, absorbs and/or dissipates on the substrate.

"Tackiness", as used herein, refers to the adhesion between two substances. For example, the more tackiness there is between two substances, the more adhesion there is between the substances.

"Keratinous substrates", as used herein, include but are not limited to, skin, hair and nails.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

As defined herein, stability is tested by placing the composition in a controlled environment chamber for 8 weeks at 250 C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 370 C., 400 C., 450 C., 500 C., and under freeze-thaw conditions. A composition is considered to lack stability if in any of these tests an abnormality that impedes functioning of the composition is observed. The skilled artisan will readily recognize an abnormality that impedes functioning of a composition based on the intended application.

"Volatile", as used herein, means having a flash point of less than about 100☐C. "Non-volatile", as used herein, means having a flash point of greater than about 100☐C.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions.

Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

Gelling Agent

According to the present invention, compositions comprising at least one gelling agent chosen from cellulose, and derivates thereof are provided. Such gelling agents are typically found in the aqueous phase of a composition.

Examples of suitable cellulose, and derivatives thereof include, but are not limited to:

cellulose polymers such as hydroxyethylcellulose, hydroxypropylcellulose, methylcellulose, ethylhydroxyethylcellulose, carboxymethylcellulose, and quaternized cellulose derivatives;

cellulosic thickeners, for example, hydroxyethylcellulose, hydroxypropylcellulose, and carboxymethylcellulose, guar gum and its derivatives, such as hydroxypropylguar, gums of microbial origin, such as xanthan gum and scleroglucan gum;

quaternized cellulose derivatives and polyacrylates containing non-cyclic amine side groups. The quaternized cellulose derivatives may include, for example:

quaternized celluloses modified with groups comprising at least one fatty chain, such as alkyl, arylalkyl, and alkylaryl groups comprising at least 8 carbon atoms, and mixtures thereof;

quaternized hydroxyethylcelluloses modified with groups comprising at least one fatty chain, such as alkyl, arylalkyl, and alkylaryl groups comprising at least 8 carbon atoms, and mixtures thereof;

polyquarternium-37 (commercially available from Cognis under the trademark name Ultragel 300 and from Ciba under the trademark name SalCARE); hydroxyalkyl cellulose polymers and alkyl hydroxyalkyl cellulose polymers such as hydroxyethyl cellulose (commercially available from Amerchol and The Dow Chemical Company and Hercules under the tradenames Cellosize and Natrosol), hydroxypropyl cellulose (commercially available from Hercules under the tradename Klucel) and cetyl hydroxyethyl cellulose (commercially available from Hercules under the tradename Natrosol);

carboxymethyl cellulose (commercially available from Hercules under the tradename Aqualon), natural or synthetic gums, and starches;

quaternized alkylhydroxyethylcelluloses containing C8-C30 fatty chains include, for instance, the products QUATRISOFT™ LM 200, QUATRISOFT™ LM-X 529-18-A, QUATRISOFT™ LM-X 529-18B (C12 alkyl), and QUATRISOFT™ LM-X 529-8 (C18 alkyl) sold by the company Amerchol, and the products CRODACEL™ QM, CRODACEL™ QL (C12 alkyl) and CRODACEL™ QS (C18 alkyl) sold by the company Croda.

Particularly preferred thickening agents are polysaccharides or polysaccharide derivatives such as hydroxyethyl cellulose, hydroxypropyl cellulose, methyl cellulose, xanthan gum, guar gum, hydroxymethylcellulose derivatives such as hydroxypropyl methylcellulose and hydroxybutyl methyl cellulose, starch and starch derivatives.

Particularly preferred rheology-modifying agents are cetyl hydroxyethyl cellulose, quaternized celluloses and hydroxyethylcelluloses.

Preferably, the gelling agent is present in the composition of the present invention in an amount ranging from about 0.1% to about 10.0% by weight, preferably from about 0.5% to about 5.0% by weight, preferably from about 1.0% to about 4.0% by weight of the total weight of the composition, including all ranges and subranges therebetween.

Oil-Soluble Polar Modified Polymer

According to the present invention, compositions comprising at least one oil-soluble polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil.

Suitable monomers for the hydrophobic homopolymers and/or copolymers include, but are not limited to, cyclic, linear or branched, substituted or unsubstituted, C2-C20 compounds such as, for example, styrene, ethylene, propylene, isopropylene, butylene, isobutylene, pentene, isopentene, isoprene, hexene, isohexene, decene, isodecene, and octadecene, including all ranges and subranges therebetween. Preferably, the monomers are C2-C8 compounds, more preferably C2-C6 compounds, and most preferably C2-C4 compounds such as ethylene, propylene and butylene.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to the present invention, the polar modified polymer is oil-soluble: that is, the polymer does not contain a sufficient amount of hydrophilic unit(s) to render the entire polymer water-soluble or oil-insoluble. According to preferred embodiments, the polar modified polymer contains the same amount of hydrophobic monomer as hydrophilic unit (1:1 ratio) or more hydrophobic monomer than hydrophilic unit. According to particularly preferred embodiments, the polar modified polymer contains 50% or less hydrophilic unit(s) (based on weight of the polymer), 40% or less hydrophilic unit(s), 30% or less hydrophilic unit(s), 20% or less hydrophilic unit(s), 10% or less hydrophilic unit(s), 5% or less hydrophilic unit(s), 4% or less hydrophilic unit(s), or 3% or less hydrophilic unit(s).

Preferably, the polar modified polymer has from about 0.5% to about 10% hydrophilic units, more preferably from about 1% to about 8% hydrophilic units by weight with respect to the weight of the polymer, including all ranges and subranges therebetween. Particularly preferred hydrophilically modified polymers are ethylene and/or propylene homopolymers and copolymers which have been modified with maleic anhydride units.

According to preferred embodiments of the present invention, the polar modified polymer is a wax. According to particularly preferred embodiments, the polar modified wax is made via metallocene catalysis, and includes polar groups or units as well as a hydrophobic backbone. Suitable modified waxes include those disclosed in U.S. patent application publication no. 20070031361, the entire contents of which is hereby incorporated by reference. Particularly preferred polar modified waxes are C2-C3 polar modified waxes.

In accordance with preferred embodiments of the present invention, the polar modified wax is based upon a homopolymer and/or copolymer wax of hydrophobic monomers and has a weight-average molecular weight Mw of less than or equal to 25 000 g/mol, preferably of 1000 to 22 000 g/mol and particularly preferably of 4000 to 20,000 g/mol, a number-average molecular weight Mn of less than or equal to 15 000 g/mol, preferably of 500 to 12 000 g/mol and particularly preferably of 1000 to 5000 g/mol, a molar mass distribution Mw/Mn in the range from 1.5 to 10, preferably from 1.5 to 5, particularly preferably from 1.5 to 3 and especially preferably from 2 to 2.5, which have been obtained by metallocene catalysis. Also, the polar modified wax preferably has a melting point above 75° C., more preferably above 90° C. such as, for example, a melting point between 90° C. and 160° C., preferably between 100° C. and 150° C., including all ranges and subranges therebetween.

In the case of a copolymer wax, it is preferable to have, based on the total weight of the copolymer backbone, 0.1 to 30% by weight of structural units originating from the one monomer and 70.0 to 99.9% by weight of structural units originating from the other monomer. Such homopolymer and copolymer waxes can be made, for example, by the process described in EP 571 882, the entire contents of which is hereby incorporated by reference, using the metallocene catalysts specified therein. Suitable preparation processes include, for example, suspension polymerization, solution polymerization and gas-phase polymerization of olefins in the presence of metallocene catalysts, with polymerization in the monomers also being possible.

Polar modified waxes can be produced in a known manner from the hompopolymers and copolymers described above by oxidation with oxygen-containing gases, for example air, or by graft reaction with polar monomers, for example maleic acid or acrylic acid or derivatives of these acids. The polar modification of metallocene polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable polar modified waxes include, but are not limited to, homopolymers and/or copolymers of ethylene and/or propylene groups which have been modified with hydrophilic units such as, for example, maleic anhydride, acrylate, methacrylate, polyvinylpyrrolidone (PVP), etc. Preferably, the C2-C3 wax has from about 0.5% to about 10% hydrophilic units, more preferably from about 1% to about 8% hydrophilic units by weight with respect to the weight of the wax, including all ranges and subranges therebetween. Particularly preferred hydrophilically modified waxes are ethylene and/or propylene homopolymers and copolymers which have been modified with maleic anhydride units.

Particularly preferred C2-C3 polar modified waxes for use in the present invention are polypropylene and/or polyethylene-maleic anhydride modified waxes ("PEMA," "PPMA," "PEPPMA") commercially available from Clariant under the trade name LICOCARE or LICOCENE, Specific examples of such waxes include products marketed by Clariant under the LicoCare name having designations such as PP207.

Other suitable polar modified polymers include, but are not limited to A-C 573 A (ETHYLENE-MALEIC ANHYDRIDE COPOLYMER; prop Point, Mettler: 106° C.) from Honeywell, A-C 596 A (PROPYLENE-MALEIC ANHYDRIDE COPOLYMER; Drop Point, Mettler: 143° C.) from Honeywell, A-C 597 (PROPYLENE-MALEIC ANHYDRIDE COPOLYMER; Drop Point, Mettler: 141° C.) from Honeywell, ZeMac® copolymers (from VERTELLUS) which are 1:1 copolymers of ethylene and maleic anhydride, polyisobutylene-maleic anhydride sold under the trade name ISOBAM (from Kuraray), polyisoprene-graft-maleic anhydride sold by Sigma Aldrich, poly(maleic anhydride-octadecene) sold by Chevron Philips Chemcial Co., poly (ethylene-co-butyl acrylate-co-maleic anhydride) sold under the trade name of Lotader (e.g. 2210, 3210, 4210, and 3410 grades) by Arkema, copolymers in which the butyl acrylate is replaced by other alkyl acrylates (including methyl acrylate [grades 3430, 4404, and 4503] and ethyl acrylate [grades 6200, 8200, 3300, TX 8030, 7500, 5500, 4700, and 4720) also sold by Arkema under the Lotader name, and isobutylene maleic anhydride copolymer sold under the name ACO-5013 by ISP.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orientation (for example, atactic, isotactic or syndiotactic along the backbone).

Preferably, the oil soluble polar modified polymer(s) represent from about 1% to about 30% of the total weight of the composition, more preferably from about 2.5% to about 15% of the total weight of the composition, and most preferably from about 5% to about 10%, including all ranges and subranges therebetween.

Water

The composition of the present invention also contains water. The water is typically present in an amount of from about 5% to about 50% by weight, such as from about 10% to about 40% by weight, such as from about 25% to about 35% by weight, including all ranges and subranges therebetween, all weights being based on the total weight of the composition. According to particularly preferred embodiments, sufficient water is present to form a water-in-oil emulsion.

Optional Ingredients

Gelling Agent

It may be desirable to employ an additional gelling agent, other than cellulose and derivatives thereof. Examples of such other gelling agents include:

water-soluble gelling polymers such as:

proteins, such as proteins of plant origin, for instance wheat proteins and soy proteins; proteins of animal origin such as keratins, for example keratin hydrolysates and sulphonic keratins;

anionic, cationic, amphoteric or nonionic chitin or chitosan polymers; and synthetic thickeners such as crosslinked homopolymers of acrylic acid and of acrylamidopropanesulphonic acid;

fatty acid amides such as coconut diethanolamide and monoethanolamide, and oxyethylenated monoethanolamide of carboxylic acid alkyl ether, and associative polymers.

Cationic associative polymers may include, but are not limited to:

cationic associative polyurethanes which may be formed from diisocyanates and from various compounds with functions containing a labile hydrogen. The functions containing a labile hydrogen may be chosen from alcohol, primary and secondary amine, and thiol functions, giving, after reaction with the diisocyanate functions, polyurethanes, polyureas, and polythioureas, respectively. The expression "polyurethanes which can be used according to the present invention" encompasses these three types of polymer, namely polyurethanes per se, polyureas and polythioureas, and also copolymers thereof. Example of such compounds include, but are not limited to, methylenediphenyl diisocyanate, methylenecyclohexane diisocyanate, isophorone diisocyanate, tolylene diisocyanate, naphthalene diisocyanate, butane diisocyanate, and hexane diisocyanate; and carboxyvinyl polymers, acrylic acid/polyallyl sucrose copolymers, polyacrylic compounds and acrylic acid/ethyl acrylate copolymers (commercially available under the CARBOPOL tradenames).

If present, such other gelling agent is preferably present in the composition of the present invention in an amount ranging from about 0.1% to about 10.0% by weight, preferably from about 0.5% to about 5.0% by weight, preferably from about 1.0% to about 4.0% by weight of the total weight of the composition.

Volatile Solvent Other than Water

The cosmetic composition of the present invention can comprise at least one volatile oil. In an embodiment of the present invention, the at least one volatile solvent may be chosen from a volatile silicone oil or a volatile non-silicone oil.

Suitable volatile silicone oils include, but are not limited to, linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (3 St) from Dow Corning | 102 | 3 |

Suitable volatile non-silicone oils may be selected from volatile hydrocarbon oils, alcohols, volatile esters and volatile ethers. Examples of such volatile non-silicone oils include, but are not limited to, volatile hydrocarbon oils having from 8 to 16 carbon atoms and their mixtures and in particular branched C8 to C16 alkanes such as C8 to C16 isoalkanes (also known as isoparaffins), isododecane, isodecane, isohexadecane, and for example, the oils sold under the trade names of Isopar or Permethyl, the C8 to C16 branched esters such as isohexyl or isodecyl neopentanoate and their mixtures. Preferably, the volatile non-silicone oils have a flash point of at least 40° C.

Non-limiting examples of volatile non-silicone oils are listed in Table 2 below.

TABLE 2

| Compound | Flash Point (° C.) |
| --- | --- |
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin C11-C13) | 62 |
| Isopar H (isoparaffin C11-C12) | 56 |

If present, the at least one volatile solvent is present in the composition in an amount of from about 20 to about 90% by weight, such as from about 30 to about 80% by weight, and from about 35 to about 75% by weight, all weights based on the total weight of the composition, including all ranges and subranges therebetween.

Non-Volatile Solvent for Oil-Soluble Polar Modified Polymer

The cosmetic composition of the present invention can comprise at least one non-volatile oil capable of dissolving the oil-soluble polar modified polymer. As used herein, the term "non-volatile" means having a boiling point of greater than about 100 degrees C.

Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula R5COOR6 in which R5 represents a linear or branched higher fatty acid residue containing from 1 to 40 carbon atoms, including from 7 to 19 carbon atoms, and R6 represents a branched hydrocarbon-based chain containing from 1 to 40 carbon atoms, including from 3 to 20 carbon atoms, with R6+R7☐10, such as, for example, Purcellin oil (cetostearyl octanoate), isononyl isononanoate, C12 to C15 alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms;

C8 to C26 fatty alcohols, for instance oleyl alcohol; and mixtures thereof.

Further, examples of hydrocarbon oils which may be used include, but are not limited to, non-polar oils such as branched and unbranched hydrocarbons and hydrocarbon waxes including polyolefins, in particular Vaseline (petrolatum), paraffin oil, squalene, squalane, hydrogenated polyisobutene, hydrogenated polydecene, polybutene, mineral oil, pentahydrosqualene, and mixtures thereof.

If present, the at least one non-volatile solvent is preferably present in the composition of the invention in an amount of from about 1% to about 20% by weight, such as from about 1.5% to about 10% by weight, such as from about 2% to about 5% by weight, all weights based on the total weight of the composition.

The composition of the present invention may also include other ingredients. Examples thereof include, but are not limited to, colorants such as dyes and pigments, co-solvents (volatile and/or non-volatile), waxes, plasticizers, preservatives, fillers, active ingredients such as those used to treat skin and hair and sunscreens.

It has been surprisingly discovered that this composition displays a high amount of moisturization to the keratinous substrate to which it has been applied and is longwearing despite the absence of silicone resins and traditional film formers. Further, the composition provides a unique comfortable texture and is stable.

The composition of the present invention may be used for any application in which it is desirable to employ a moisturizing, long wearing product, and which is stable, easily spreadable, and comfortable to apply.

The present invention is further described in terms of the following non-limiting examples. Unless otherwise indicated, all parts and percentages are on a weight-by-weight percentage basis.

Example

A cosmetic composition was prepared containing the below-disclosed ingredients.

| | |
|---|---|
| isohexadecane | 2.25 |
| isododecane | 35.50 |
| PP207 * | 6.75 |
| polyglyceryl-2 triisostearate | 2.50 |
| DI Water | 40.00 |
| cellulose | 1.50 |
| TITANIUM DIOXIDE | 7.82 |
| IRON OXIDES | 1.46 |
| IRON OXIDES | 0.52 |
| IRON OXIDES | 0.20 |
| DISODIUM EDTA | 0.20 |
| propylene glycol | 0.50 |
| PHENOXY-2 ETHANOL | 0.40 |
| CHLORPHENESIN | 0.20 |
| ETHYL PARABEN | 0.20 |
| TOTAL | 100.00 |

* PP207 is a linear polypropylene-ethylene-maleic anhydride copolymer wax commercially available from Clariant under the tradename LICOCARE PP207 LP 3349.

Procedure

1. In container A, PP207 was melted in the isohexadecane and isododecane until fully dissolved. The temperature was brought to 900 C.
2. While maintaining the temperature, the emulsifier and pigment grind were added to container A until fully dissolved.
3. In a separate container B, water, cellulose, and preservatives were mixed at room temperature.
4. The contents of container B were added to the contents of container A slowly at high sheer (~700 rpm).
5. Heat was maintained at 700 C-800 C for 20 minutes while maintaining high sheer mixing.
6. The mixture was cooled to room temperature while mixing.

What is claimed is:

1. A composition comprising:
   (a) at least one cellulosic gelling agent selected from the group consisting of polyquaternium-10, hydroxypropyl methylcellulose, hydroxybutyl methylcellulose, and mixtures thereof;
   (b) at least one oil-soluble polar modified polymer consisting of polypropylene and/or polyethylene, modified with maleic anhydride units, and having a weight-average molecular weight of less than or equal to 25 000 g/mol and a melting point above 75° C.; and
   (c) water,
   wherein the composition is in the form of an emulsion.

2. The composition of claim 1, wherein the oil-soluble polar modified polymer is present in an amount of from about 3% to about 20% by weight, based on the weight of the composition.

3. The composition of claim 1, wherein the oil-soluble polar modified polymer is present in an amount of from about 1% to about 30% by weight, based on the weight of the composition.

4. The composition of claim 1, wherein water is present in an amount of from about 5 to about 50% by weight, based on the weight of the composition.

5. The composition of claim 1, further comprising at least one non-volatile oil.

6. The composition of claim 5, wherein the non-volatile oil is present in an amount of from about 1 to about 20% by weight, based on the weight of the composition.

7. The composition of claim 1, further comprising at least one colorant.

8. The composition of claim 1, wherein the cellulosic gelling agent is present in an amount of from about 0.1% to about 10.0% by weight of the total weight of the composition.

9. The composition of claim 2, wherein the cellulosic gelling agent is present in an amount of from about 0.1% to about 10.0% by weight of the total weight of the composition.

10. The composition of claim 3, wherein the cellulosic gelling agent is present in an amount of from about 0.1% to about 10.0% by weight of the total weight of the composition.

11. The composition of claim 4, wherein the cellulosic gelling agent is present in an amount of from about 0.1% to about 10.0% by weight of the total weight of the composition.

12. The composition of claim 1, in the form of a water-in-oil emulsion.

13. A method of making-up a keratinous substrate comprising applying onto the substrate in an amount sufficient to make up the substrate a composition comprising:
   (a) at least one cellulosic gelling agent selected from the group consisting of polyquaternium-10, hydroxypropyl methylcellulose, hydroxybutyl methylcellulose, and mixtures thereof;
   (b) at least one oil-soluble polar modified polymer consisting of polypropylene and/or polyethylene, modified with maleic anhydride units, and having a weight-average molecular weight of less than or equal to 25 000 g/mol and a melting point above 75° C.; and
   (c) water,
   wherein the composition is in the form of an emulsion.

14. The composition of claim 1, wherein the weight-average molecular weight of the oil-soluble polar modified polymer is from 1,000 to 22,000 g/mol.

15. The composition of claim 1, wherein the melting point of the oil-soluble polar modified polymer is between 90° C. and 160° C.

16. The composition of claim 1, wherein the oil-soluble polar modified polymer has from about 0.5% to about 10% maleic anhydride units by weight with respect to the weight of the oil soluble polar modified polymer.

17. The composition of claim 1, wherein the oil-soluble polar modified polymer has from about 1% to about 8% maleic anhydride units by weight with respect to the weight of the oil soluble polar modified polymer.

18. The composition of claim 2, wherein the oil-soluble polar modified polymer has from about 0.5% to about 10% maleic anhydride units by weight with respect to the weight of the oil soluble polar modified polymer.

19. The composition of claim 3, wherein the oil-soluble polar modified polymer has from about 1% to about 8% maleic anhydride units by weight with respect to the weight of the oil soluble polar modified polymer.

\* \* \* \* \*

UNITED STATES PATENT AND TRADEMARK OFFICE
CERTIFICATE OF CORRECTION

PATENT NO. : 8,828,366 B2
APPLICATION NO. : 12/825614
DATED : September 9, 2014
INVENTOR(S) : Hy S. Bui et al.

Page 1 of 1

It is certified that error appears in the above-identified patent and that said Letters Patent is hereby corrected as shown below:

On the title page, Item (75), the residence information for inventor Mohamed Kanji should read as follows: --Mohamed Kanji, Edison, NJ (US);--.

In the Claims

Column 10, line 11, "75° C.;" should read --75° C;--;

line 57, "75° C.;" should read --75° C;--; and line 64, "90° C." should read --90° C--.

Signed and Sealed this
Twenty-third Day of December, 2014

Michelle K. Lee
*Deputy Director of the United States Patent and Trademark Office*